United States Patent [19]
Bletsos et al.

[11] Patent Number: 5,801,278
[45] Date of Patent: Sep. 1, 1998

[54] LOW WATER DIAMINE-DICARBOXYLIC ACID SALT PREPARATION

[75] Inventors: Ioannis V. Bletsos, Vienna, W. Va.; Constantine D. Papaspyrides, Athens, Greece

[73] Assignee: E. I. du Pont de Nemours and Companh, Wilmington, Del.

[21] Appl. No.: 813,737

[22] Filed: Mar. 7, 1997

[51] Int. Cl.⁶ .................. C07C 55/00; C07C 209/00; C08G 69/26

[52] U.S. Cl. .................. 562/590; 564/468; 528/335; 528/332; 528/336; 528/310; 528/322

[58] Field of Search ................. 528/335, 332, 528/336, 310, 322; 562/590; 564/468

[56] References Cited

U.S. PATENT DOCUMENTS

| | | | |
|---|---|---|---|
| 4,442,260 | 4/1984 | Larsen | 524/845 |
| 4,925,914 | 5/1990 | Dolden et al. | 528/336 |
| 4,933,192 | 6/1990 | Darling et al. | 426/98 |

*Primary Examiner*—Gary Geist
*Assistant Examiner*—Rosalynd Keys

[57] ABSTRACT

The invention provides a process for directly manufacturing a diamine/dicarboxylic acid salt with a low water content. The process includes reacting a diamine with a dicarboxylic acid to form a diamine/dicarboxylic acid salt. The reaction of the diamine and the dicarboxylic acid is carried out in the presence of about 0.5% to about 25% by weight water, based on the weight of the reaction mixture, while providing conditions in the reaction mixture such that the reaction mixture is in substantially solid particulate form.

11 Claims, No Drawings

LOW WATER DIAMINE-DICARBOXYLIC ACID SALT PREPARATION

FIELD OF THE INVENTION

The present invention relates to the direct preparation of diamine/dicarboxylic acid salts with a low water content.

TECHNICAL BACKGROUND OF THE INVENTION

Poly(hexamethylene adipamide) (nylon 6,6) polymer is typically manufactured commercially by first making an aqueous salt solution from its monomers hexamethylenediamine and adipic acid. The diamine is supplied as a dilute aqueous solution so that the resulting hexamethylene diammonium adipate (nylon 6,6 salt) solution usually contains water in the range of about 50% by weight. This solution is then used as a starting material and initial reaction medium for the solution/melt polymerization of nylon 6,6. While techniques are known for precipitating the salt from the solution such as by adding a non-solvent for the salt to the solution, e.g., isopropanol, such processes require the subsequent recovery of the non-solvent from the solution.

SUMMARY OF THE INVENTION

The invention provides a process for directly manufacturing a diamine/dicarboxylic acid salt with a low water content. The process includes contacting a diamine with a dicarboxylic acid to provide a reaction mixture in which the diamine and the dicarboxylic acid react to form a diamine/dicarboxylic acid salt. The contacting of the diamine and the dicarboxylic acid is carried out in the presence of about 0.5% to about 25% water by weight based on the weight of the reaction mixture while providing conditions in the reaction mixture such that the reaction mixture is in substantially solid particulate form.

Preferably, the contacting of the diamine with the dicarboxylic acid is carried out in the presence of about 2% to about 10%, most preferably at about 2% to about 5%, water by weight based on the weight of the reaction mixture.

In accordance with a preferred form of the present invention, maintaining the reaction mixture in substantially solid particulate form is performed by providing sufficient heat transfer from the reaction mixture when exposed to an ambient temperature less than the melting points of the diamine, the dicarboxylic acid, the diamine/dicarboxylic acid salt and intermediate reaction products in the reaction mixture. Preferably, the reaction mixture is formed by exposing the dicarboxylic acid to the ambient temperature and subsequently adding the diamine, optionally containing up to about 10% water combined therewith, in liquid (molten) form.

The process provides a diamine/dicarboxylic acid salt directly with a low water content which is advantageous for use as a starting material for the manufacture of polyamides such as nylon 66. When the water content is within the preferred range, the salt can be recovered as a stable, free-flowing powder which is easily shipped for use at remote locations. For the manufacture of nylon 66, the salt produced by the invention is less dangerous than the 90% hexamethylene diamine solution which is a typical form for shipping the diamine to keep it in the liquid state at moderate temperatures. The salt is also generally easier to handle than adipic acid.

DETAILED DESCRIPTION

The invention involves the reaction of a diamine with a dicarboxylic acid to form a diamine/dicarboxylic acid salt. Any of a wide variety of diamine/dicarboxylic acid salts may be made by this process. Such diamine/dicarboxylic acid salts are useful as starting materials for the manufacture of polyamides of the type which are made from aliphatic or alicyclic diamine and aliphatic or alicyclic dicarboxylic acid monomers. In addition, the invention is also useful to make salts for polyamide manufacture which have diamine or dicarboxylic acid components which are aromatic. Aromatic diamines useful in this invention are, for example, isophenylene diamine and paraphenylene diamine. Useful aromatic diacids are, for example, isophthalic acid and terephthalic acid.

The salts made according to the present process can be useful for the manufacture of homopolyamides where only one diamine and one dicarboxylic acid are used. Salts can also be made using the invention where a mixture of two or more diamines is reacted with one or a mixture of diacids or where a mixture of two or more diacids is reacted with one or a mixture of diamines. Aminocarboxylic acids, e.g., aminocaproic acid (the nylon 6 monomer unit), are also used in copolyamides. Minor quantities of one or more such aminocarboxylic acids, can be added to the reaction mixture also. If desired, small quantities of branching agents such as tris(2-aminoethyl)amine can also be incorporated into the resulting salt by addition to the reaction mixture.

The primary reactions which take place in a process according to the invention may be summarized by Equation I as follows:

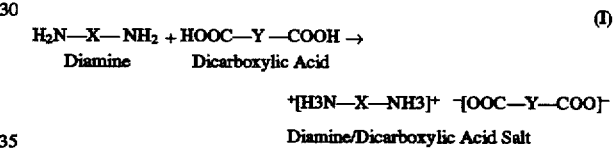

In the equation, X is an aliphatic, alicyclic, or aromatic group and the diamine is preferably selected from the group consisting of aliphatic, alicyclic, and aromatic diamines having 2 to 16 carbon atoms. Y also represents an aliphatic, alicyclic, and aromatic group and the dicarboxylic acid is preferably selected from the group consisting of aliphatic, alicyclic, and aromatic dicarboxylic acids having 2 to 16 carbon atoms.

Depending on the end use of the salt, the relative molar quantities of the diamine and dicarboxylic acid added to the reaction mixture can be adjusted as desired. For example, additional diamine can be incorporated into a salt for the manufacture of a polyamide used for fiber manufacture in which increase dyeability using anionic dyes is desired.

The invention is advantageously used to make salts for polyamides which are primarily aliphatic or alicyclic in character, i.e., less than 15% of the amide linkages of the resulting polymer are attached to two aromatic rings. Such polyamides are commonly referred to as nylons and are usually melt-processable. Such polyamides include those made from aliphatic diacids and aliphatic diamines such as poly(hexamethylene adipamide) (nylon 6,6) and poly(butylene adipamide) (nylon 4,6) and their copolymers. A particularly preferred salt is made from the reaction of hexamethylenediamine and adipic acid and is referred to as nylon 6,6 salt in the examples which follow.

The reaction of the diamine and the dicarboxylic acid is carried out under conditions so that the reaction mixture is in substantially solid particulate form. Since the reaction of a diamine with a dicarboxylic acid is strongly exothermic, there is a propensity, if the temperature is not controlled, for the reaction mixture to form a paste and agglomerate into a single mass rather than to remain in the substantially solid particulate form. By "substantially solid particulate form" is meant that discrete particles exist throughout the reaction although there may be some temporary, localized paste formation or softening on the particles but without significant agglomeration. Under conditions which promote the formation of a paste, it is believed that the monomers begin to react to form oligomers rather than forming the desired salt. If very high temperatures occur, degradation or other undesirable reactions may occur.

Maintaining substantially solid particulate form is preferably achieved by providing sufficient heat transfer from the reaction mixture when exposed to an ambient temperature less than the melting points of the diamine, said dicarboxylic acid, the diamine/dicarboxylic acid salt and intermediate reaction products in the reaction mixture. This is advantageously accomplished by employing a temperature well below room temperature such as by contacting the reaction mixture with a cryogenic medium. Preferred cryogenic media include particulate dry ice and liquid nitrogen.

To maintain the reaction mixture in particulate form and to assist with heat and mass transfer, the mixture should be agitated. In order for the solid reaction to proceed at a fast rate, it is desirable for the particulate reactants in the reaction mixture to be finely divided. The mixing should be sufficiently vigorous that heat transfer to the cryogenic medium substantially prevents paste formation.

Unlike conventional diamine/dicarboxylic acid salt formation processes which are carried out in aqueous solutions containing approximately 50% water by weight, the water content of the reaction mixture in the process of the invention is at a much lower level, that is, about 0.5 to about 25% by weight based on the weight of the reaction mixture. While the salt formation reaction may occur to some extent with no water being added to the reaction mixture, quantities of water in accordance with the invention favor the formation of the salt and improve its homogeneity. Preferably, the water content is about 2% to about 10% by weight, most preferably at about 2 to about 5% by weight. When the water content is within the preferred range, the diamine/dicarboxylic acid salts are preferably recovered as a free-flowing powder to facilitate subsequent handling.

A particularly preferred way of carrying out the invention is to expose the dicarboxylic acid in powder form to a low ambient temperature, i.e., contacting it with the cryogenic medium, and subsequently adding a diamine, optionally containing up to about 10% water combined therewith, in liquid (molten) form. This is particularly advantageous since some diamines such as hexamethylene diamine are available commercially as concentrated solutions, e.g., 91.3%, which will provide the preferred quantity of water to the reaction mixture. Using such amine solutions, very slight, if any, heating is required to maintain these solutions in liquid form for ease of addition to the reaction mixture. Moreover, the rate of addition of the liquid diamine can be easily controlled to match the heat transfer conditions, i.e., the liquid addition can be adjusted to a sufficiently low rate to prevent the formation of a paste.

The diamine/dicarboxylic acid salts, which can be stored and shipped with a low water content, are useful starting materials for the manufacture of polyamide polymers. The salts can be used to make conventional aqueous solutions containing about 50% water by weight for use in known commercial processes for the manufacture of polyamide polymers. The salts can also be used in a low temperature polymerization process as taught in U.S. Pat. No. 5,403,910, which is incorporated herein by reference.

The following example is intended to illustrate the invention without limiting the invention to the embodiments described. Percentages are by weight unless otherwise indicated. Percentages of water in the reaction mixture are reported by weight based on the total weight of the reaction mixture including the water present but excluding any cryogenic media in contact with the reaction mixture.

EXAMPLE 1

A batch procedure was used to make a nylon 66 salt employing a double-arm kneading mixer with sigma blades sold by Werner and Pfleiderer, 663 East Cresent Avenue, Ramsey, N.J., 07446 ("Werner"). This mixer was suitably modified with rubber gaskets to increase the resistance to pressure and prevent the evaporation of hexamethylene diamine so as to meet the needs of the process (mixing chamber: 1.50 L) and was used due to its capability to create the torque required to effect better homogenization of the reactants employed. As indicated in Table 1, a number of runs were performed. The procedure for Runs 1–4 included loading 146 g (1 mole) adipic acid powder and the cryogenic medium (when used) into the mixer. 127 g of an aqueous solution containing 91.3% HMD (116 g HMD—1 mole and 11 g water) heated to 45° C. was added through a funnel into the mixer over a period of 15 minutes. The resulting mixture was then blended for 1 hour. The water content of the reaction mixture is about 4%. In Run 5, no water was added to the reaction mixture and the equivalent molar amount of the diamine in powder form was added to the dicarboxylic acid and dry ice already loaded in the mixer.

Table 1 reports amine and carboxyl ends of the product, the difference between carboxyl ends and amine ends, percent water added, cryogenic media used and the form of the product (powder or paste). The homogeneity of the product samples was evaluated by taking the standard deviation of five (5) pH measurements (pH determined in 9.5% aqueous solution.)

Run No. 1 is not an example of the invention since it is performed without a cryogenic medium and it results in the formation of a paste rather than a free-flowing powder. The homogeneity was not good based on the percentage standard deviation of the pH measurements (percent standard deviation, p.s.d.=19.5%).

Runs numbered 2–4 exemplify the process of the present invention. In Runs No. 2 and No. 3 dry ice was employed as the cryogenic medium. In Run No. 2, the quantity of dry ice was arbitrarily chosen to the level of half the grams of the adipic acid, i.e., 73 g. In Run No. 3 the double quantity of dry ice was used, i.e., 146 g. In Run No. 4 liquid nitrogen was used (half the mixing chamber). In these three runs, the diamine water solution was added to the mixture of the adipic acid powder already blended with dry ice or liquid nitrogen.

Based on the amine and carboxylic group analysis, Runs No. 2 and No. 3 show that a practically balanced salt is produced under the conditions employed. The percent standard deviation of the pH measurements shows the products of runs 2 and 3 to be homogenous. (Run 2, p.s.d.=3.6%; Run 3, p.s.d.=1.50%). Infrared spectroscopy of the products reveals a typical spectrum of the nylon salt 6,6 including a very characteristic peak at 2200 $cm^{-1}$.

Run No. 4 demonstrates that liquid nitrogen can be used as the cryogenic medium. In the procedure used, adipic acid and liquid nitrogen are quickly blended in the closed chamber and the diamine water solution was added. However, under the conditions employed, some adipic acid powder was lost out of the chamber when the liquid nitrogen was vigorously evaporated. This explains the reduced value of the carboxyl group concentration of the end-product. Nevertheless, standard deviation of pH measurements again reveals a homogeneous product (p.s.d.=0.6). The infrared spectrum of the product reveals a typical spectrum of the nylon 6,6 salt.

Run No. 5 is a comparative example in which solid hexamethylenediamine was ground to grains in a mortar and pestle and was added to a blend of dry ice (146 g) and the adipic acid in the sigma mixer. In this case, no water was added at all. Standard deviation of pH (p.s.d=20.7%) and infrared spectroscopy indicate the product to be inhomogenous and the amine and carboxyl group analysis also shows an unbalanced salt structure.

pH measurements were made using a sufficient quantity of wet sample to make a 9.5% aqueous solution. For standard deviation, the number of samples, n=5.

Infrared spectroscopy was done on a dry sample in nujol.

What is claimed is:

1. A process for preparing a diamine/dicarboxylic acid salt comprising contacting a diamine with a dicarboxylic acid to provide a reaction mixture in which said diamine and said dicarboxylic acid react to form a diamine/dicarboxylic acid salt, said contacting being carried out in the presence of about 0.5% to about 25% water by weight based on the weight of the reaction mixture and while providing conditions in said reaction mixture such that said reaction mixture is in substantially solid particulate form.

2. The process of claim 1 wherein said contacting is carried out in the presence of about 2% to about 10% water by weight based on the weight of the reaction mixture.

TABLE 1

| SAMPLE | $NH_2$ (meq/g) | COOH (meq/g) | [COOH—$NH_2$] (meq/g) | % S.D. pH | % Water added by weight | Cryogenic Media | Form[1] |
|---|---|---|---|---|---|---|---|
| Commercial Nylon 66 Salt | 7.62 | 7.73 | 0.11 | — | — | — | PO |
| Run 1 (Comparative) | — | — | — | 19.5 | 4 | No | PA |
| Run 2 (Invention) | 7.32 | 7.42 | 0.10 | 3.6 | 4 | $CO_2$ | PO |
| Run 3 (Invention) | 7.20 | 7.56 | 0.36 | 1.5 | 4 | $CO_2$ (X2) | PO |
| Run 4 (Invention) | 7.84 | 7.00 | −0.84 | 0.6 | 4 | $N_2$ | PO |
| Run 5 (Comparative) | 6.93 | 7.91 | 0.98 | 20.7 | None added | $CO_2$ (X2) | PO |

[1]Form (PO=Powder, PA = Paste)

TEST METHODS

Where "dry sample" is referred to in the following test methods, drying was performed by heating the sample for 2 hours at 50° C. "Wet sample" refers to a sample of the reaction product that did not undergo drying. Samples are taken so as to avoid "dead" points in the mixing chamber where, especially in the absence of cryogenic medium, the reacting mass tended to be accumulated.

Amine and acid end groups were determined by potentiometric titration using a METROHM 670 TITROPROCESSOR with a BECKMAN FUTURA PLUS combination electrode using the filling solution as received (4M KCl saturated with AgCl). 0.1 Grams of a dry sample were weighed into a 150 ml beaker to which was added a polytetrafluoroethylene-coated (polytetrafluoroethylene is sold by DuPont under the trademark TEFLON®) stirring bar and 100 ml of 75 volume % ethanol/water. The solution was stirred until the sample was dissolved. The solution was titrated for amine ends with 0.1N hydrochloric acid until at least 1 ml beyond the amine break. The same solution was then back-titrated through two end points with 0.1N sodium hydroxide for acid end groups. Blanks were run for both titrations using 100 ml of 75 volume % ethanol/water. The amine ends and acid ends were calculated according to the equations below:

Amine end groups (meq/g):

$$\frac{[ml\ HCl(sample) - ml\ HCl(blank)] \times N(HCl)}{grams\ of\ sample}$$

Acid end groups (meq/g):

$$\frac{[ml\ NaOH(2^{nd}\ break) - ml\ NaOH(1^{st}\ break)] - ml\ NaOH(blank)] \times N(NaOH)}{grams\ of\ sample}$$

3. The process of claim 1 wherein said contacting is carried out in the presence of about 2% to about 5% water by weight based on the weight of the reaction mixture.

4. The process of claim 1 wherein said providing conditions such that said reaction mixture is in substantially solid particulate form is performed by providing sufficient heat transfer from said reaction mixture when exposed to an ambient temperature less than the melting points of said diamine, said dicarboxylic acid, said diamine/dicarboxylic acid salt and intermediate reaction products in said reaction mixture.

5. The process of claim 4 wherein said reaction mixture is formed by exposing said dicarboxylic acid to said ambient temperature and subsequently adding said diamine as a aqueous liquid solution.

6. The process of claim 1 further comprising contacting said reaction mixture with dry ice particles.

7. The process of claim 1 further comprising forming said reaction mixture in liquid nitrogen.

8. The process of claim 2 further comprising recovering said diamine/dicarboxylic acid salt from said process as a free-flowing powder.

9. The process of claim 1 wherein said diamine is selected from the group consisting of aliphatic, alicyclic, and aromatic diamines having 2 to 16 carbon atoms.

10. The process of claim 1 wherein said dicarboxylic acid is selected from the group consisting of aliphatic, alicyclic, and aromatic dicarboxylic acids having 2 to 16 carbon atoms.

11. The process of claim 1 wherein said diamine is hexamethylenediamine and said dicarboxylic acid is adipic acid.

* * * * *